United States Patent

Dau

Patent Number: 5,518,756
Date of Patent: May 21, 1996

[54] POWDER MIXTURE

[76] Inventor: Peter C. Dau, 229 Lynchford Road, Farnborough, United Kingdom, GU14 6BF

[21] Appl. No.: 236,036
[22] Filed: May 2, 1994
[51] Int. Cl.$^6$ ............................ A23G 3/00; A23P 1/00; A23L 1/05
[52] U.S. Cl. .................... 426/659; 426/658; 426/572; 426/610
[58] Field of Search .................... 426/659, 658, 426/572, 610

[56] References Cited

U.S. PATENT DOCUMENTS

| | | | |
|---|---|---|---|
| 3,874,924 | 4/1975 | Sands et al. | 426/659 |
| 3,961,980 | 6/1976 | Dunshee | 426/659 |
| 4,037,000 | 7/1977 | Burge et al. | 426/659 |
| 4,135,005 | 2/1979 | Cheng . | |

FOREIGN PATENT DOCUMENTS

| | | |
|---|---|---|
| 760765 | 2/1953 | United Kingdom . |
| 930461 | 4/1958 | United Kingdom . |
| 930462 | 6/1958 | United Kingdom . |
| 1444729 | 6/1969 | United Kingdom . |
| 1501484 | 1/1978 | United Kingdom . |
| 2204223 | 3/1988 | United Kingdom . |
| 2209917 | 1/1989 | United Kingdom . |
| WO88/08254 | 11/1988 | WIPO . |

OTHER PUBLICATIONS

Report under Section 17 on Application No. GB 9123089.6.
Report under Section 17 on Applicvation No. GB 9222736.2.

Primary Examiner—Donald E. Czaja
Assistant Examiner—Choon P. Koh
Attorney, Agent, or Firm—Nixon & Vanderhye

[57] ABSTRACT

A powder mixture for mixing with water on a greased surface to form a sugar-based paste for forming into cake decorations, comprises:

25 kg icing sugar (including up to 3% cornflour);
250 g carboxy methyl cellulose (E466);
350 g xanthum gum (E415);
90 g of gum arabic (E414);
700 g cornflour; and
250 g powdered glucose.

10 Claims, No Drawings

POWDER MIXTURE

DESCRIPTION

This invention relates to a powder mixture for mixing with water on a greased surface to form a sugar-based paste for forming into cake decorations.

The International School of Sugarcraft Book Two Advanced by Nicholas Lodge, published in 1988 by Merehurst Press, London, describes a complex recipe for producing quality flower paste having a desirable white colour which can be rolled out thinly and which has qualities of plasticity when so rolled appropriate to enable it to be formed into fine petal shapes, which will retain that plasticity for a time sufficient for the formation of such fine shapes and which will result in strong moulded flower petals. In carrying out this recipe a gelatine solution is formed by sprinkling powdered gelatine into water and leaving it to sponge, placing it over a pan of hot water to warm it, stirring in liquid glucose and white fat; whilst at the same time stirring together sugar and starch, sprinkling gum tragacanth either alone or with carboxy methyl cellulose over the starch and sugar mixture, and heating, whereafter albumen and the gelatine solution are added to the warmed mixture of sugar starch and gum, the resultant being mixed slowly until all the ingredients are combined into a beige paste, and then mixed at high speed until the paste is white and stringy. That takes five to ten minutes. The white and stringy product is then placed in an airtight container and refrigerated for at least twenty four hours before being ready for use. It retains its plasticity, even when rolled out thinly, sufficiently long for it to be worked because it retains viscous liquid elements incorporated in it during its preparation.

A quicker and simpler method of forming flower paste is also described on the same page but the resultant paste is inferior in quality, any flowers formed with it will be both less delicate and less strong than flowers formed with the paste produced by the longer, complex recipe described above. The short method involves kneading sugar paste and gum tragacanth together and adding a small amount of white fat to get an elastic consistency. The sugar paste is a commercially available product comprising liquid glucose and gum. It is intended for use for covering cakes so that it must be soft enough to be cut, and must remain so for as long as the cake is fresh enough to eat which may be an extended period of time.

GB-A-2209917 discloses a powder comprising sugar, gelatine, gum tragacanth, albumen, cornflour and glucose which can be obtained for use as an instant mix to form a flower paste by the simple addition of water. However the qualities of colour, plasticity, ability to be rolled out thinly whilst retaining its plasticity for sufficient time for it to be worked into the required shape, and strength of the final fine shapes formed of it, of the resultant paste are not as good as those of the flower paste produced by the long, complex recipe described above.

An object of this invention is to provide a powder which can be formed into a paste having the desirable qualities of the flower paste produced by the long, complex recipe described above to the same extent, simply by the addition of water to the powder on a greased surface.

Up to now, gelatine has been thought to be an essential ingredient of such a powder. I have appreciated that it is the use of gelatine that causes the problem of loss of plasticity when the paste is rolled out thinly, that being because it is insoluble in cold water. On the other hand I have found that albumen is a useable alternative to gelatine but it is expensive.

The essence of my invention is that I use neither gelatine nor liquid glucose whereas I use one or more edible gums or carboxy methyl cellulose as a plasticiser.

According to my invention there is provided a substantially dry powder mixture for mixing with water on a greased surface to form a kneadable sugar-based paste for forming into fine petal shapes and similar fine, structurally complex cake decorations, comprising powdered sugar and plasticiser means consisting of substances derived from a non-animal source. Preferably the powder mixture also includes powdered starch, which preferably is refined starch, and/or a water retention and crystal formation inhibiting powder such as powdered glucose (dextrose monohydrate).

In a preferred embodiment the plasticiser means comprise a mixture of two edible gums, one of which is less water absorbent than the other.

The use of two edible gums having different water absorbent characteristics enables the resultant sugar based paste to be formed without there being too much water or without it being too dry so that it is a more plastic paste than a paste made from a powder mixture including a single edible gum such as xanthum gum, and so that it feels a better paste to handle. A paste made from a powder mixture in which this invention is embodied has the advantage that it does not include any animal products in contrast to those which include gelatin or albumen.

The preferred powdered sugar is icing sugar. The plasticiser means may comprise xanthum gum, which is a corn sugar gum, and a smaller amount by weight of acacia gum such as gum arabic (E414). Alternatively carboxy methyl cellulose may be used alone as the plasticiser means, or in combination with either tragacanth gum or acacia gum, or in combination with a larger amount by weight of xanthum gum.

One example of a powder in which this invention is embodied is described now by way of example. The ingredients of the powder were:

25 kg icing sugar (including up to 3% cornflour)

250 g carboxy methyl cellulose (E466)

350 g xanthum gum (E415)

90 g of gum arabic (E414)

700 g cornflour 250 g powdered glucose (dextrose monohydrate)

The carboxy methyl cellulose, the xanthum gum, the gum arabic, the cornflour and the powdered glucose were mixed together. The resultant mixture was blended with the 25 kg icing sugar with a small amount of an anti-caking agent, such as cornflour or magnesium carbonate (504), by a known blending technique so that the mixture was evenly and finely distributed throughout the icing sugar.

To form the powder mixture into sugar paste, about 100 g of the powder mixture is placed in a greased basin, about 20 ml of water is added and mixed into the powder in the basin whereafter about a further 100 g of powder is kneaded into the mixture of powder and water in the basin. The resultant paste is white, can be rolled out thinly without loss of plasticity, and can be used to form delicate, fine but strong decorative shapes.

The powder mixture is formed into paste in a greased basin because the grease which will be incorporated in the paste will slow down drying and that helps the paste to retain its plasticity. It is drying that leads to a loss of plasticity and the presence of the powdered glucose also retards drying, as well as inhibiting formation of crystals.

The cornflour ingredient contributes to smoothness in paste formed from the powder mixture.

I claim:

1. A substantially dry powder mixture for mixing with water on a greased surface to form a kneadable sugar-based paste for forming into fine petal shapes and similar fine, structurally complex cake decorations, comprising powdered sugar, plasticizer means comprising at least one edible gum, and devoid of substances derived from an animal source.

2. A powder mixture according to claims 1, wherein the plasticiser means comprise xanthum gum and a smaller amount of carboxy methyl cellulose.

3. A substantially dry powder mixture according to claim 2, wherein the plasticiser means comprises carboxy methyl cellulose in combination with tragacanth gum and acacia gum.

4. A substantially dry powder mixture according to claim 2, wherein the plasticiser means comprise a mixture of two edible gums, one of which is less water absorbent than the other.

5. A substantially dry powder mixture according to claim 1, wherein said plasticiser means comprises carboxymethyl cellulose.

6. A substantially dry powder mixture according to claim 1 and including starch.

7. A substantially dry powder mixture according to claims 6 wherein the starch is refined starch.

8. A substantially dry powder mixture according to claim 1, including a water retention and crystal formation inhibiting powder.

9. A substantially dry powder mixture according to claim 8, wherein the water retention and crystal formation inhibiting powder is powdered glucose.

10. A substantially dry powder mixture according to claim 1, wherein the powdered sugar is icing sugar.

* * * * *